United States Patent [19]

Davis

[11] Patent Number: 4,825,002

[45] Date of Patent: Apr. 25, 1989

[54] DECONTAMINATION OF (HYDROCARBYLTHIO) AROMATIC AMINES

[75] Inventor: Robert L. Davis, Baton Rouge, La.

[73] Assignee: Ethyl Corporation, Richmond, Va.

[21] Appl. No.: 115,859

[22] Filed: Nov. 2, 1987

Related U.S. Application Data

[63] Continuation-in-part of Ser. No. 878,813, Jun. 26, 1986, abandoned.

[51] Int. Cl.$^4$ .................. C07C 149/02; C07C 149/04; C07C 149.42
[52] U.S. Cl. .................................... 564/438; 546/293; 548/484; 548/541; 564/428; 564/429; 564/430; 564/437

[58] Field of Search ............... 564/438, 437, 430, 428, 564/429; 546/293; 548/484, 541

[56] References Cited

U.S. PATENT DOCUMENTS 4,559,182 12/1985 Grotta ................................ 564/438
4,594,453 6/1986 Ranken et al. ..................... 548/541

Primary Examiner—Richard L. Raymond
Assistant Examiner—Ba Trinh
Attorney, Agent, or Firm—Patricia J. Hogan

[57] ABSTRACT

A Lewis acid contaminant is removed from a (hydrocarbylthio)aromatic amine by mixing a solid alkali metal hydroxide with a solution of the Lewis acid in the amine, preferably at about 110°–120° C., and then filtering the solids from the mixture.

11 Claims, No Drawings

4,825,002

DECONTAMINATION OF (HYDROCARBYLTHIO) AROMATIC AMINES

CROSS REFERENCE TO RELATED APPLICATION

This application is a continuation-in-part of copending application Ser. No. 878,813, filed June 26, 1986, now abandoned.

FIELD OF INVENTION

This invention relates to (hydrocarbylthio)aromatic amines and more particularly to a process for decontaminating them.

BACKGROUND

As disclosed in U.S. Pat. No. 4,594,453 (Ranken et al.), it is known that (hydrocarbylthio)aromatic amines can be prepared by reacting an aromatic amine with a hydrocarbyl disulfide in the presence of a catalytic amount of a Lewis acid. The Lewis acid contaminant can be removed by diluting the product with an organic liquid such as toluene, washing with an aqueous acid or base, and then removing the diluent and water. However, this decontamination technique is bothersome, uneconomical, and apt to be particularly unsatisfactory when the amine is to be used in an application in which even small amounts of water cannot be tolerated.

SUMMARY OF INVENTION

An object of this invention is to provide a novel process for decontaminating (hydrocarbylthio)aromatic amines.

Another object is to provide such a process which is simple, economical, and capable of removing Lewis acid contaminants without the use of water.

These and other objects are attained by intimately mixing at least about two molar proportions of a solid alkali metal hydroxide with a solution of one molar proportion of a Lewis acid in a (hydrocarbylthio)aromatic amine in the absence of a solubilizing agent for the alkali metal hydroxide and filtering the solids from the mixture.

DETAILED DESCRIPTION (Hydrocarbylthio)aromatic amines that can be decontaminated in the practice of the invention are Lewis acid-contaminated aromatic compounds bearing one or more hydrocarbylthio substituents on a carbocyclic or heterocyclic ring (e.g., a benzene, naphthalene, pyrrole, pyridine, indole, etc., ring) which has an amino nitrogen in the ring and/or bears one or more amino groups on the ring and which may bear additional substituents, such as chloro, fluoro, alkyl, alkoxy, aryl, aryloxy, alkaryl, or aralkyl substituents, e.g., all of the (hydrocarbylthio)aromatic amines that may be prepared by the process of Ranken et al., the teachings of which are incorporated herein in toto by reference.

Thus, the amines include, e.g., the mono- and polyhydrocarbylthio compounds prepared by reacting a hydrocarbyl disulfide (e.g., methyl, ethyl, propyl, n-butyl, sec-butyl, t-butyl, 2-chloropentyl, cyclopentyl, cyclohexyl, phenyl, benzyl, p-tolyl, or pchlorophenyl disulfide) with an aromatic amine (e.g., 4,4,-methylenedianiline, 1,3-dimethylpyrrole, 1-methylpyrrole, 2-aminobiphenyl, 4-phenoxyaniline, 7-methylindole, aniline, 4-butylaniline, 4-methylaniline, 4-chloroaniline, 2-ethylaniline, N-methylaniline , 1,5-diaminonaphthalene, 2,6-diaminopyridine , 1,2-, 1,3-, and 1,4-diaminobenzenes, 2,4- and 2,6-diaminotoluenes, 2,6-diamino-1-ethylbenzene, etc.) in the presence of a Lewis acid, such as a boron, aluminum, ferrous, ferric, cuprous, cupric, zinc, cadmium, lead, cobaltous, mercurous, or mercuric chloride, bromide, or iodide, a reactive metal (e.g., aluminum), a metal alkyl (e.g., triethylaluminum, diethylaluminum chloride, etc.), etc.

In a preferred embodiment of the invention, the solution that is treated in the practice of the invention is a solution of a boron or metal halide Lewis acid in one or more mono- or polyhydrocarbylthio-substituted aromatic diamines, especially such diamines wherein the hydrocarbylthio groups are alkylthio groups containing 1-6 carbons. This solution is usually the reaction product resulting from a Ranken-type process, although a solution obtained, e.g., by adding a Lewis acid to a preformed (hydrocarbylthio)aromatic amine can also be successfully treated.

The alkali metal hydroxide may be lithium, sodium, potassium, rubidium, or cesium hydroxide but is preferably sodium hydroxide. To permit intimate admixture it is used in particulate form, e.g., as a powder, flakes, or granules; and it is conveniently employed as a bed of particles over which the contaminated amine can flow. The amount employed should be such as to provide at least about two, preferably at least about four, hydroxyl groups for each metal atom or equivalent in the Lewis acid. There does not appear to be any maximum to the amount that may be used except for the maximum that may be set by economic considerations.

In the decontamination process, the solid alkali metal hydroxide is intimately mixed with the Lewis acid/amin solution at any suitable temperature, generally at ambient temperature or at a higher temperature up to about 120° C. and preferably at about 110°–120° C., until the Lewis acid concentration has been reduced to an acceptable level. The time required varies with the particular hydroxide and temperature used and with the ultimate Lewis acid concentration sought but is typically in the range of about 1–8 hours.

The process is conducted in the absence of water or other solubilizing agent for the alkali metal hydroxide; and, in a preferred embodiment of the invention, it is also conducted in the absence of any diluent. However, the major advantage of the invention, i.e., lack of contamination with water, can also be achieved when the Lewis acid/amine solution is a diluted solution wherein the diluent is an aromatic liquid which is miscible with the amine. Such diluents include, e.g., hydrocarbyl disulfides such as those used in the syntheses of the (hydrocarbylthio)aromatic amines; other amines; aromatic hydrocarbons such as toluene, xylene, etc.; and halogenated hydrocarbons, such as chloroform, bromoform, methylene chloride, etc. An advantage of the use of a diluent is that it can sometimes make the filtration step easier to accomplish; a disadvantage is its adding two steps—the addition of the diluent and its removal—to the process.

The invention is advantageous as a simple, economical method of removing a Lewis acid contaminant from a (hydrocarbylthio)aromatic amine without the use of water. The effectiveness of the solid alkali metal hydroxide in the process is surprising, since the hydroxide is not soluble in the amine, and other hydroxides, such as calcium hydroxide, are relatively ineffective when used in solid form.

The following examples are given to illutrate the invention and are not intended as a limitation thereof.

EXAMPLE I

A solution of about 3 mol % of cuprous iodide in about 93 mol % of di(methylthio) derivatives, about 3 mol % of mono(methylthio) derivatives, and about 1 mol % of tri(methylthio) derivatives was prepared by reacting a commercial toluenediamine containing 80% 2,4-diaminotoluene and 20% 2,6-diaminotoluene with methyl disulfide in the presence of cuprous iodide. After excess methyl disulfide was stripped from the reaction mixture, solid sodium hydroxide was mixed with the solution to provide a mixture containing four mols of sodium hydroxide per mol of cuprous iodide, and the mixture was heated at 110°–120° C. for eight hours. Samples were taken periodically, filtered, and analyzed to determine the amount of copper remaining in the amine.

| Time (hrs.) | Wt. % Cu |
| --- | --- |
| 0 | 1.3 |
| 1 | 0.06 |
| 2 | 0.05 |
| 4 | 0.04 |
| 6 | 0.04 |
| 8 | 0.04 |

EXAMPLE II

Example I was repeated except that the amount of sodium hydroxide mixed with the crude amine was six mols per mol of cuprous iodide. Analyses showed that the amount of copper in the product was reduced to 0.04 wt. % in only one hour and remained at that level during subsequent heating.

EXAMPLE III

Example I was repeated except that amount of sodium hydroxide mixed with the crude maine was only three mols per mol of cuprous iodide and heating was maintained for only two hours. After two hours the amount of copper in the product was reduced to 0.2 wt. %.

EXAMPLE IV

Example I was repeated except that the sodium hydroxide was replaced with potassium hydroxide. The results of the analyses are shown below.

| Time (hrs.) | Wt. % Cu |
| --- | --- |
| 0 | 1.3 |
| 1 | 0.1 |
| 2 | 0.2 |
| 4 | 0.07 |
| 6 | 0.07 |
| 8 | 0.08 |

EXAMPLE V

Example I was essentially repeated except that the crude amine was one that had been prepared in the presence of a mixture of cuprous iodide and boron trifluoride etherate. The results of the analyses are shown below.

| Time (hrs.) | Wt. % Cu | Wt. % B |
| --- | --- | --- |
| 0 | 0.67 | 0.012 |
| 1 | 0.17 | 0.009 |
| 2 | 0.14 | 0.006 |
| 4 | 0.16 | 0.004 |
| 6 | 0.14 | 0.003 |
| 8 | 0.12 | 0.001 |

It is obvious that many variations can be made in the products and processes set forth above without departing from the spirit and scope of this invention.

What is claimed is:

1. A process which comprises separating a Lewis acid from a (hydrocarbylthio)aromatic amine by intimately mixing at least about two molar proportions of a solid alkali metal hydroxide with a solution of one molar proportion of a Lewis acid in a (hydrocarbylthio)aromatic amine in the absence of a solubilizing agent for the alkali metal hydroxide and filtering the solids from the mixture.

2. The process of claim 1 wherein the alkali metal hydroxide is sodium hydroxide.

3. The process of claim 1 wherein the Lewis acid is a boron or metal halide or mixture thereof.

4. The process of claim 3 wherein the Lewis acid is cuprous iodide.

5. The process of claim 1 wherein the (hydrocarbylthio)aromatic amine comprises at least one aromatic diamine bearing one or more alkylthio groups containing 1–6 carbons.

6. The process of claim 1 wherein the (hydrocarbylthio)aromatic amine is a mixture of methylthio-substituted toluenediamines.

7. The process of claim 1 wherein at least about four molar proportions of alkali metal hydroxide are mixed with the solution.

8. The process of claim 1 wherein the mixture is maintained at about 110°–120° C. until the Lewis acid concentration in the solution has been reduced.

9. The process of claim 1 wherein the alkali metal hydroxide is mixed with the Lewis acid/amine solution in th absence of a diluent.

10. The process of claim 1 wherein the alkali metal hydroxide is mixed with the Lewis acid/amine solution in the presence of a diluent.

11. The process of claim 1 wherein at least about four molar proportions of solid sodium hydroxide are mixed with a solution of one molar proportion of a metal halide Lewis acid in a mixture of methylthio-substituted toluenediamines, the mixture is heated at 110°–120° C., and the solids are then filtered from the mixture.

* * * * *